(12) United States Patent
Hu et al.

(10) Patent No.: US 11,737,732 B2
(45) Date of Patent: Aug. 29, 2023

(54) ULTRASONIC IMAGING SYSTEM AND ULTRASONIC IMAGING METHOD FOR TRANSDUCER TRANSLATION SELECTION AND SPECIFIC POSITIONING RESCAN

(71) Applicant: GE Precision Healthcare LLC, Wauwatosa, WI (US)

(72) Inventors: Wei Hu, Wuxi (CN); Houbing Liu, Wuxi (CN); Min Zhong, Nuxi (CN); Jing Ni, Wuxi (CN); Chunyan Qi, Wuxi (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 5 days.

(21) Appl. No.: 17/504,091

(22) Filed: Oct. 18, 2021

(65) Prior Publication Data
US 2022/0133275 A1 May 5, 2022

(30) Foreign Application Priority Data

Oct. 30, 2020 (CN) .......................... 202011197422.4

(51) Int. Cl.
  *A61B 8/00* (2006.01)
  *G01S 7/52* (2006.01)
  *G01S 15/89* (2006.01)

(52) U.S. Cl.
  CPC ............ *A61B 8/469* (2013.01); *A61B 8/4461* (2013.01); *G01S 7/52026* (2013.01); *G01S 7/52036* (2013.01); *G01S 15/8911* (2013.01)

(58) Field of Classification Search
  CPC ... A61B 8/469; A61B 8/4461; G01S 7/52026; G01S 7/52036; G01S 15/8911
  See application file for complete search history.

(56) References Cited

U.S. PATENT DOCUMENTS

| | | | |
|---|---|---|---|
| 6,675,038 B2 | 1/2004 | Cupples | |
| 2010/0210946 A1* | 8/2010 | Harada | A61B 8/4281 600/443 |
| 2011/0306886 A1* | 12/2011 | Daft | G01S 15/8915 600/459 |
| 2015/0094588 A1* | 4/2015 | Summers | A61B 8/0825 600/445 |
| 2015/0094589 A1* | 4/2015 | Chen | G01S 15/899 600/459 |
| 2016/0174934 A1* | 6/2016 | Cong | A61B 8/4254 600/459 |
| 2017/0128045 A1* | 5/2017 | Roundhill | A61B 8/5269 |
| 2019/0125301 A1* | 5/2019 | Jago | A61B 8/0825 |

* cited by examiner

*Primary Examiner* — Shahdeep Mohammed
*Assistant Examiner* — Amal Aly Farag (57) ABSTRACT

An ultrasonic imaging method and an ultrasonic imaging system are provided herein. The ultrasonic imaging system includes: a scanning assembly having an ultrasonic transducer to send ultrasonic signals to a tissue to be scanned and acquire a plurality of ultrasonic echo signals at a plurality of positions; a processor to receive the plurality of ultrasonic echo signals acquired at the plurality of positions, and generate an ultrasonic image corresponding to each of the plurality of positions; a display to display the ultrasonic images; and a user input unit to select the ultrasonic image corresponding to any specific position and send an input signal that is configured to control movement of the ultrasonic transducer, driven by a driving device, to the specific position. Also provided in the present invention is an ultrasonic imaging method using the system.

16 Claims, 8 Drawing Sheets

ULTRASONIC IMAGING SYSTEM AND ULTRASONIC IMAGING METHOD FOR TRANSDUCER TRANSLATION SELECTION AND SPECIFIC POSITIONING RESCAN

CROSS-REFERENCE TO RELATED APPLICATIONS

This application claims priority based on Chinese application No. 202011197422.4, filed on Oct. 30, 2020, the contents of which are incorporated herein by reference.

TECHNICAL FIELD OF THE INVENTION

The present invention relates to the field of medical imaging, and in particular, to an ultrasonic imaging system and an ultrasonic imaging method.

BACKGROUND OF THE INVENTION

Ultrasonic imaging is one of the important means for imaging the interior of the body of a person to be scanned. Generally, ultrasonic imaging systems use ultrasonic transducers to convert electrical energy into ultrasonic pulses. The ultrasonic pulses are sent to the interior of the body of the person to be scanned, and echo signals are generated. The echo signals are received by transducer elements, and are then converted to electrical signals. The electrical signals are processed by a specialized processing device to schedule a desired ultrasonic image.

Ultrasonic imaging systems use important applications in scanning of many body organs. For example, a full-field breast ultrasonic scanning device may be used to image breast tissue in one or a plurality of planes. During full-field breast ultrasonic scanning, it is usually necessary for a scanning assembly to apply a certain pressure to a tissue to be scanned (e.g., a breast) to press the tissue to be scanned for imaging, and then an ultrasonic transducer is moved for ultrasonic scanning. The scanning imaging process typically take a certain amount of time to acquire a large number of ultrasonic images. After scanning is completed, a user may check the acquired ultrasonic images. When it is found that there are unsatisfactory images or images that need to be emphatically observed (e.g., suspected pathology) in the ultrasonic images, it is necessary to rescan the tissue to be scanned. Such a process would take a lot of time.

BRIEF SUMMARY OF THE INVENTION

In an embodiment, an ultrasonic imaging system includes a scanning assembly including a driving device and an ultrasonic transducer. The driving device driving the ultrasonic transducer to move to a plurality of positions on a surface of a tissue to be scanned, and the ultrasonic transducer sending ultrasonic signals to the tissue to be scanned at the plurality of positions and acquiring a plurality of ultrasonic echo signals at the plurality of positions. The ultrasonic imaging system includes a processor for receiving the plurality of ultrasonic echo signals acquired at the plurality of positions, and generating an ultrasonic image corresponding to each of the plurality of positions based on the ultrasonic echo signals. The ultrasonic imaging system includes a display for displaying the ultrasonic images and a user input unit for selecting an ultrasonic image corresponding to any specific position of the plurality of positions and sending an input signal that is configured to control movement of the ultrasonic transducer, driven by the driving device, to the specific position.

In an embodiment, an ultrasonic imaging method for use with an ultrasonic imaging system including a scanning assembly including a driving device and an ultrasonic transducer, wherein the driving device is configured to drive the ultrasonic transducer to move to a plurality of positions on a surface of a tissue to be scanned, a processor, a display, and a user input unit, the method including brining the scanning assembly close to a surface of a tissue to be scanned. The method including controlling the driving device to drive the ultrasonic transducer to move to a plurality of positions on the surface of the tissue to be scanned, and at the same time, controlling the ultrasonic transducer to send ultrasonic signals to the tissue to be scanned a the plurality of positions and acquire a plurality of ultrasonic echo signals at the plurality of positions. The method including controlling the processor to receive the plurality of ultrasonic echo signals acquired at the plurality of positions, and generating an ultrasonic image corresponding to each of the plurality of positions based on the ultrasonic echo signals. The method including selecting, by the user input unit, an ultrasonic image corresponding to any specific position of the plurality of positions and sending an input signal that is configured to control movement of the ultrasonic transducer, driven by the driving device, to the specific position.

BRIEF DESCRIPTION OF THE DRAWINGS

The present invention will be better understood by reading the following description of non-limiting embodiments with reference to the accompanying drawings, where.

DETAILED DESCRIPTION OF THE INVENTION

Specific implementations of the present invention will be described in the following. It should be noted that during the specific description of the implementations, it is impossible to describe all features of the actual implementations in detail in present invention for the sake of brief description. It should be understood that in the actual implementation of any of the implementations, as in the process of any engineering project or design project, a variety of specific decisions are often made in order to achieve the developer's specific objectives and meet system-related or business-related restrictions, which will vary from one implementation to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. "First," "second" and similar words used in the present invention and the claims do not denote any order, quantity or importance, but are merely intended to distinguish between different constituents. "One," "a(n)," and similar terms are not meant to be limiting, but rather denote the presence of at least one. The term "include," "comprise," or a similar term is intended to mean that an element or article that appears before "include" or "comprise" encompasses an element or article and equivalent elements that are listed after "include" or "comprise," and does not exclude other elements or articles. The term "connect," "connected," or a similar term is not limited to a physical or mechanical connection, and is not limited to a direct or indirect connection.

Figure 1:
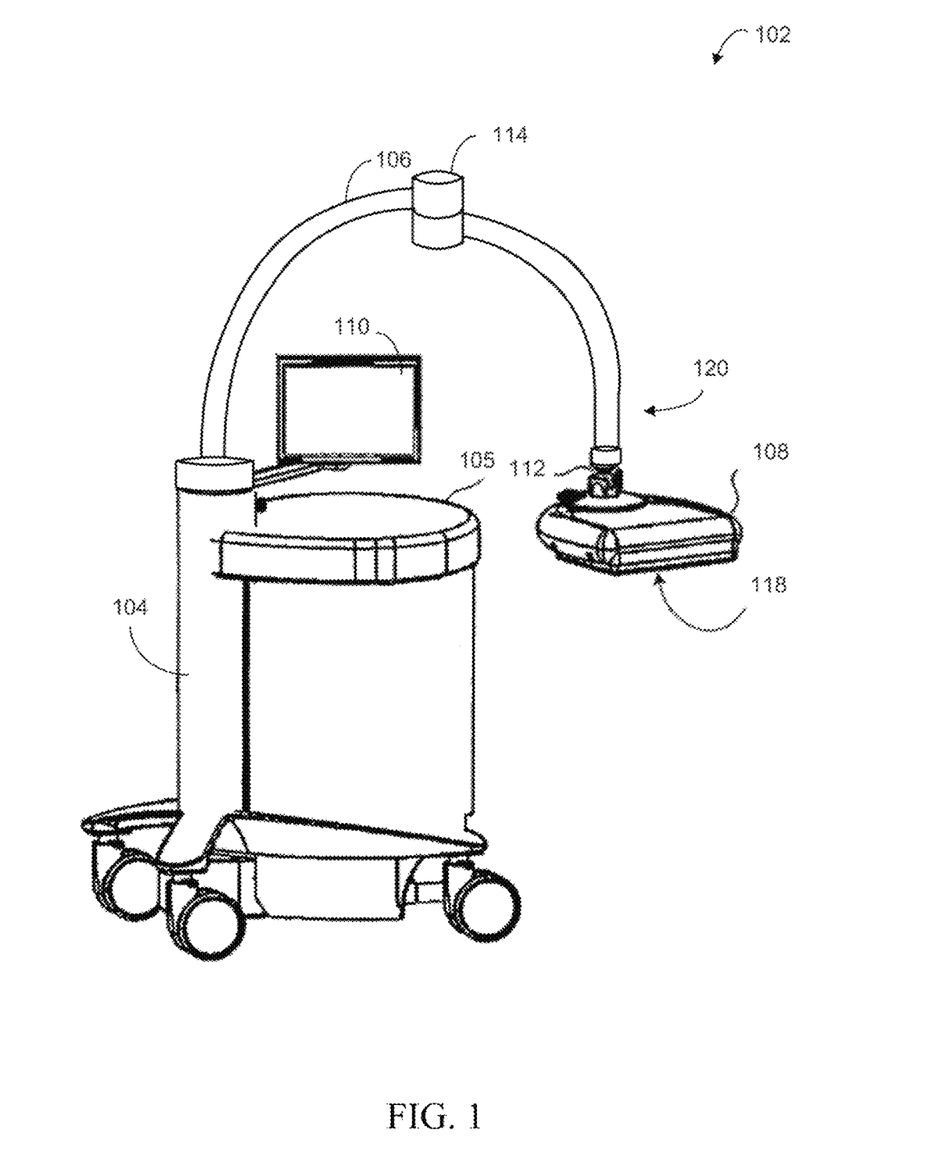
FIG. 1 is a perspective view of an ultrasonic imaging system according to some embodiments of the present invention.

FIG. 1 shows a perspective view of an ultrasonic imaging system 102 (hereinafter also generally referred to as an imaging system 102) according to some embodiments. An ultrasonic imaging system 102 body may of a main device, a display 110, an adjustable arm 106, and a scanning assembly 108. Wherein the main device may include a body frame 104, an ultrasonic processor housing 105, and an ultrasonic processor inside the housing 105. The specific structure of each component will be illustrated in detail below.

The body frame 104, the ultrasonic processor housing 105 containing the ultrasonic processor, a movable and adjustable support arm (for example, an adjustable arm) 106 including a hinge joint 114, the scanning assembly 108 connected to a first end 120 of the adjustable arm 106 by means of a ball and socket connector (for example, a ball joint) 112, and the display 110 connected to the body frame 104. The display 110 is connected to the body frame 104 at a joining point where the adjustable arm 106 enters the body frame 104. Since the display 110 is directly connected to the body frame 104 rather than the adjustable arm 106, the display 110 does not affect the weight of the adjustable arm 106 and a balancing mechanism of the adjustable arm 106. In one example, the display 110 may rotate in horizontal and transverse directions (for example, rotatable around a central axis of the body frame 104), but cannot move vertically. In an alternative example, the display 110 may also be vertically movable. Although FIG. 1 depicts the display 110 connected to the body frame 104, in other examples, the display 110 may be connected to different components of the imaging system 102, such as, connected to the ultrasonic processor housing 105, or positioned away from the imaging system 102.

In one embodiment, the adjustable arm 106 is configured and adapted such that the pressing/scanning assembly 108 (i) is neutrally buoyant in space, or (ii) has a light net downward weight (for example, 1-2 kg) for pressing the breast, while allowing easy user operation. In an alternative embodiment, the adjustable arm 106 is configured so that the scanning assembly 108 is neutrally buoyant in space during positioning of a scanner on a tissue of a patient. Then, after the scanning assembly 108 is positioned, internal components of the imaging system 102 may be adjusted to apply a desired downward weight for pressing the breast and improving image quality. In one example, the downward weight (for example, a force) may be in a range of 2-11 kg.

As described above, the adjustable arm 106 includes the hinge joint 114. The hinge joint 114 divides the adjustable arm 106 into a first arm portion and a second arm portion. The first arm portion is connected to the scanning assembly 108 and the second arm portion is connected to the body frame 104. The hinge joint 114 allows the second arm portion to rotate relative to the second arm portion and the body frame 104. For example, the hinge joint 114 allows the scanning assembly 108 to translate transversely and horizontally, but not vertically, relative to the second arm portion and the body frame 104. In such manner, the scanning assembly 108 can rotate toward the body frame 104 or away from the body frame 104. However, the hinge joint 114 is configured to allow the entire adjustable arm 106 (for example, the first arm portion and the second arm portion) to move vertically together as a whole (for example, translating upward and downward along with the body frame 104).

The scanning assembly 108 may include a film assembly 118 having a film that is in a substantially tensioned state to be at least partially attached, for pressing the breast. The film assembly 118 has a bottom surface for contacting the breast, and when the bottom surface is in contact with the breast, the transducer sweeps over a top surface of the film to scan the breast. In one example, the film is a tensioned fabric sheet.

The film assembly 118 may further include an outer frame and a film. The film is fixedly arranged in the outer frame, and the outer frame is detachably connected to the scanning assembly. In an ultrasonic imaging process performed by the ultrasonic imaging system, one surface of the film can be at least partially in contact with an ultrasonic transducer, and another surface of the film is at least partially in contact with a tissue to be scanned. Such an arrangement can ensure that the ultrasonic transducer transmits and receives signals with less attenuation, and can fix the breast to be scanned to facilitate scanning.

Optionally, the adjustable arm may include a potentiometer (not shown) to allow position and direction sensing performed by the pressing/scanning assembly 108, or may use other types of position and direction sensing (such as gyroscope, magnetic, optical, and radio frequency (RF)). A fully functional ultrasonic engine may be provided within the ultrasonic processor housing 105, and is configured to drive the ultrasonic transducer, and generate volumetric breast ultrasound data from a scan in conjunction with related position and orientation information. In some examples, volumetric scan data may be transmitted to another computer system by using any of a variety of data transmission methods known in the art so as to be further processed, or the volumetric scan data may be processed by the ultrasonic engine. A general-purpose computer/processor integrated with the ultrasonic engine may further be provided for general user interface and system control. The general-purpose computer may be a self-contained stand-alone unit, or may be remotely controlled, configured, and/or monitored by remote stations connected across networks.

Figure 2:
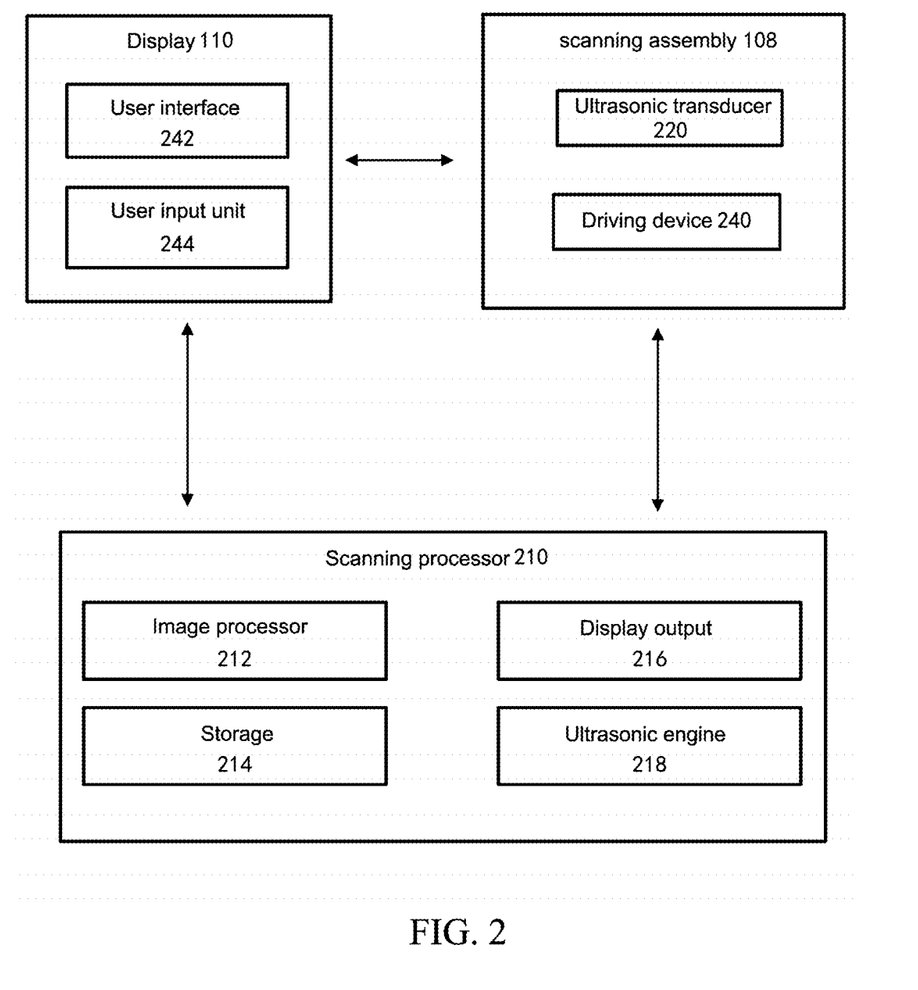
FIG. 2 is a schematic block diagram of various system parts according to some embodiments of the present invention.

FIG. 2 is a block diagram 200 schematically showing various system components of the imaging system 102, including a scanning assembly 108, a display 110, and a scanning processor 210. In one example, the scanning processor 210 may be included within the ultrasonic processor housing 105 of the imaging system 102. As shown in the embodiment of FIG. 2, the scanning assembly 108, the display 110, and the scanning processor 210 are independent components that communicate with each other; however, in some embodiments, one or more of these components may be integrated (for example, the display and the scanning processor may be included in a single component).

First, referring to the scanning assembly 108, the scanning assembly 108 at least includes an ultrasonic transducer 220 and a driving device 240. The ultrasonic transducer 220 includes a transducer array of transducer elements, such as piezoelectric elements, which converts electrical energy into ultrasonic waves and then detects reflected ultrasonic waves. The structure of the driving device 240 will be described in detail below.

The scanning assembly 108 may communicate with the scanning processor 210 to send raw scan data to an image processor. The scanning assembly 108 may optionally communicate with the display 110 so as to indicate a user to reposition the scanning assembly as described above, or to receive information from the user (via a user input unit 244).

Turning now to the scanning processor 210, the the scanning processor includes an image processor 212, a memory 214, display output 216, and an ultrasonic engine 218. The ultrasonic engine 218 may drive activation of the transducer elements of the transducer 220, and in some embodiments, the driving device 240 may be activated. Furthermore, the ultrasonic engine 218 may receive raw image data (e.g., ultrasonic echoes) from the scanning assembly 108. The raw image data may be sent to the image processor 212 and/or a remote processor (e.g., via a network), and processed to form a displayable image of a tissue sample. It should be understood that in some embodiments, the image processor 212 may be included in the ultrasonic engine 218.

Information may be transmitted from the ultrasonic engine 218 and/or the image processor 212 to the user of the imaging system 102 via a display output 216 of the scanning processor 210. In an example, the user of the scanning device may include an ultrasonic technician, a nurse, or a physician such as a radiologist. For example, a processed image of scanned tissue may be sent to the display 110 via the display output 216. In another example, information related to parameters of the scan (such as progress of the scan) may be sent to the display 110 via the display output 216. The display 110 may include a user interface 242 configured to display images or other information to the user. Furthermore, the user interface 242 may be configured to receive an input from the user (such as by means of the user input unit 244), and send the input to the scanning processor 210. In one example, the user input unit 244 may be a touch screen of the display 110. However, other types of user input mechanisms are also possible, such as a mouse, a keyboard, and the like.

The scanning processor 210 may further include the memory 214. The storage 214 may include movable and/or permanent devices, and may include an optical memory, a semiconductor memory, and/or a magnetic memory. The storage 214 may include a volatile, non-volatile, dynamic, static, read/write, read only, random access, sequential access, and/or additional memory. The storage 214 may store non-transitory instructions executable by a controller or processor (such as the controller 218 or the image processor 212) so as to perform one or more methods or routines as described below. The storage 214 may store raw image data received from the scanning assembly 108, processed image data received from the image processor 212 or the remote processor, and/or additional information.

Figure 3:
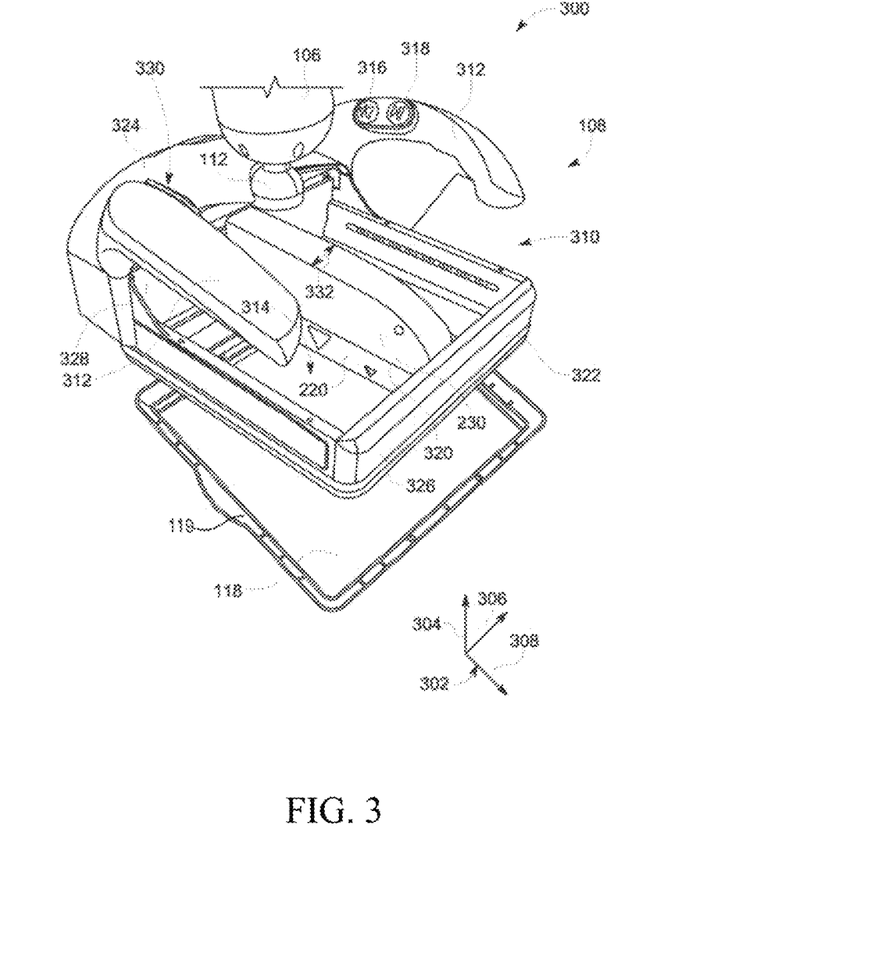
FIG. 3 is a perspective view of a scanning assembly according to some embodiments of the present invention.

Referring to FIG. 3, a schematic diagram 300 of an isometric view of the scanning assembly 108 connected to the adjustable arm 106 is shown. The schematic diagram 300 includes a coordinate system 302, and the coordinate system 302 includes a vertical axis 304, a horizontal axis 306, and an abscissa axis 308.

The scanning assembly 108 includes a housing 310, the transducer module 220, and the module receiver 230. The housing 310 includes a frame 322 and a handle portion 324, and the handle portion includes two handles 312. The two handles 312 oppose each other across a transverse axis of the scanning assembly 108, and the transverse axis is centered on the adjustable arm 106 and defined relative to the transverse axis 308. The frame 322 is rectangular, and an inner periphery of the frame 322 defines an opening 314. The opening 314 provides space (e.g., a void volume), for translating the module receiver 230 and the transducer module 220 during a scanning process. In another example, the frame 322 can have another shape, such as a square having the square opening 314. In addition, the frame 322 has a thickness defined between an inner periphery and an outer periphery of the frame 322.

The frame 322 includes four sets of side walls (e.g., a set including inner and outer side walls, the inner side walls defining the opening 314). In particular, the frame 322 includes a front side wall 326 and a rear side wall 328, the rear side wall 328 is directly connected to the handle portion 324 of the housing 310, and the front side wall 326 is opposite to the rear side wall 328 with respect to the horizontal axis 306. The frame 322 further includes right and left side walls, the corresponding side walls opposing each other and both being in a plane defined by the vertical axis 304 and the transverse axis 308.

The frame 322 of the housing 310 further includes a top side and a bottom side, and the top side and the bottom side are defined relative to the vertical axis 304. The top side faces the adjustable arm 106. The film 118 is disposed across the opening 314. More specifically, the film 118 is connected to the bottom side of the frame 322. In an example, the film 118 is a diaphragm that remains tensioned across the opening 314. The film 118 may be made from a flexible but non-stretchable material, and the material is thin, waterproof, durable, highly acoustically transparent, resistant to chemical corrosion, and/or biocompatible. As described above, the bottom surface of the film 118 may contact a tissue (e.g., a breast) during scanning, and an upper surface of the film 118 may at least partially contact the transducer module 220 during scanning. As shown in FIG. 3, the film 118 is permanently connected to a hard-housing holding portion 119 surrounding the periphery of the film 118. The holding portion 119 is connected to the bottom side of the frame 322. In one example, the holding portion 119 can be fastened to a lip-like edge on the bottom side of the frame 322 of the housing 310, so that the film 118 does not become unconnected during scanning, but is still removably connected to the frame 322. The film 118 may not be permanently connected to the hard-housing holding portion 119, and thus the film 118 may be connected to the frame 322 without the hard-housing holding portion 119. Instead, the film 118 may be directly and removably connected to the frame 322.

The handle portion 324 of the housing 310 includes the two handles 312 for moving the scanning assembly 108 in space and positioning the scanning assembly 108 on a tissue (e.g., on a patient). In an alternative embodiment, the housing 310 may not include the handle 312. In an example, the handle 312 may be integrally formed with the frame 322 of the housing 310. In another example, the handle 312 and the frame 322 may be formed separately and then mechanically connected together to form the entire housing 310 of the scanning assembly 108.

As shown in FIG. 3, the scanning assembly 108 is connected to the adjustable arm 106 by means of the ball joint 112 (e.g., a ball and socket connector). Specifically, a top dome portion of the handle portion 324 is connected to the ball joint 112. The top of the handle portion 324 includes a depression forming a socket, and a ball of the ball joint 112 is fit in the socket. The ball joint 112 is movable in multiple directions. For example, the ball joint 112 provides rotational motion of the scanning assembly relative to the adjustable arm 106. The ball joint 112 includes a locking mechanism for locking the ball joint 112 in place, thereby holding the scanning assembly 108 stationary relative to the adjustable arm 106. Furthermore, the ball joint 112 may also be configured to only rotate but not to move in multiple directions, such as oscillating.

Additionally, as shown in FIG. 3, the handle 312 of the handle portion 324 includes buttons for controlling scanning and adjusting the scanning assembly 108. Specifically, a first handle of the handles 312 includes a first weight adjustment button 316 and a second weight adjustment button 318. The first weight adjustment button 316 may reduce a load applied to the scanning assembly 108 from the adjustable arm 106. The second weight adjustment button 318 may increase a load applied to the scanning assembly 108 from the adjustable arm 106. Increasing the load applied to the scanning assembly 108 may increase the pressure and the amount of pressing applied to the tissue on which the scanning assembly 108 is placed. Furthermore, increasing the load applied to the scanning assembly increases the effective weight of the scanning assembly on the tissue to be scanned. In one example, increasing the load may press a tissue of a patient, such as a breast. In such way, varying amounts of pressure (e.g., load) may be applied consistently with the scanning assembly 108 during scanning in order to obtain high quality images by using the transducer module 220.

Prior to the scanning process, a user (e.g., an ultrasonic technician or physician) may position the scanning assembly 108 on a patient or a tissue. Once the scanning assembly 108 is properly positioned, the user may adjust a weight (e.g., adjusting an amount of pressing) of the scanning assembly 108 on the patient by using the first weight adjustment button 316 and/or the second weight adjustment button 318. Then, the user may initiate the scanning process by means of additional control on the handle portion 324 of the housing 310. For example, as shown in FIG. 3, the second handle of the handles 312 includes two additional buttons 330 (not separately shown). The two additional buttons 330 may include a first button for initiating a scan (e.g., once the scanning assembly has been placed on the tissue/patient and an amount of pressing has been selected) and a second button for stopping the scan. In one example, once the first button is selected, the ball joint 112 may be locked, thereby stopping transverse and horizontal movement of the scanning assembly 108.

The module receiver 230 is positioned within the housing 310. Specifically, the module receiver 230 is mechanically connected to a first end of the housing 310 at a rear side wall 328 of the frame 322, and the first end is closer to the adjustable arm 106 than a second end of the housing 310. The second end of the housing 310 is located at a front side wall 326 of the frame 322. In one example, the module receiver 230 is connected to the first end by means of a protruding portion of the module receiver 230, the protruding portion is connected to the motor 230, and the protruding portion is connected to the motor of the module receiver 230.

As described above, the housing 310 is configured to remain stationary during scanning. In other words, once the weight applied to the scanning assembly 108 is adjusted by means of the adjustable arm 106 and then the ball joint 112 is locked, the housing 310 may remain in the resting position without translating in the horizontal or transverse direction. However, the housing 310 may still translate vertically as the adjustable arm 106 move vertically.

Instead, the module receiver 230 is configured to translate relative to the housing 310 during scanning. As shown in FIG. 3, the module receiver 230 translates horizontally along a horizontal axis 306 relative to the housing 310. The motor of the module receiver 230 may slide the module receiver 230 along an upper surface of the first end of the housing 310.

The transducer module 220 is removably connected to the module receiver 230. Therefore, during scanning, the transducer module 220 and the module receiver 230 translate horizontally. During scanning, the transducer module 220 sweeps horizontally across the breast under the control of the motor of the module receiver 230, and at the same time, a contact surface of the transducer module 220 contacts the film 118. The transducer module 220 and the module receiver 230 are connected together at a module interface 320. The module receiver 230 has a width 332 that is the same as a width of the transducer module 220. In an alternative embodiment, the width 332 of the module receiver may be different from the width of the transducer module 220. In some embodiments, the module interface 320 includes a connector between the transducer module 220 and the module receiver 230, and the connector includes mechanical and electrical connections.

Figure 4:
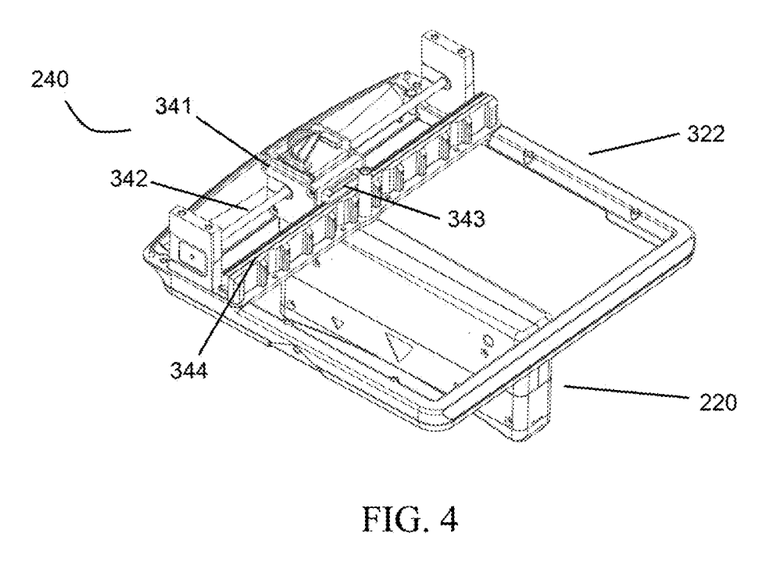
FIG. 4 is a schematic diagram of a connection relationship between a frame and an ultrasonic transducer of a scanning assembly according to some embodiments of the present invention.

Referring to FIG. 4, a schematic diagram of a connection relationship between the frame 322 and the ultrasonic transducer 220 in the scanning assembly 108 according to some embodiments of the present invention is shown. The drawing omits a structure of a housing that accommodates the driving device 240 in the frame 322 of the scanning assembly 108, and a structure including a controller and a circuit board and arranged in the frame 322, so as to clearly illustrate the specific structure of the driving device 240. The driving device 240 is partially accommodated in the frame 322 (the specific housing is not shown), and is connected to the ultrasonic transducer 220 so as to be able to drive the ultrasonic transducer 220 to move. The driving device 240 may include a motor 341 and a lead screw 342. The lead screw 342 is arranged in the frame 322. For example, two ends thereof may be fixedly connected to two side walls of the frame 322. The motor 341 is connected to the ultrasonic transducer 220. For example, the motor 341 may be fixedly connected to one end of the ultrasonic transducer 220 by means of a screw structure. The motor 341 is movably connected to the lead screw 342 so as to drive the ultrasonic transducer 220 to move.

In a manner shown in FIG. 4, the motor 341 drives the ultrasonic transducer 220 to perform reciprocating movement in a direction of the lead screw by means of rotation of an internal output shaft in different directions (e.g., clockwise or counterclockwise direction) or by using the output shaft to drive a gear to movably connect the lead screw 342, thereby automatically performing ultrasonic scanning. It should be noted that other motion modes are also allowed. For example, the ultrasonic transducer 220 is driven to rotate around a certain center of circle. Although the internal structure of the motor 341 is not directly shown in FIG. 4, those skilled in the art should know that all modes that establish the movable connection between the motor 341 and the lead screw 342 are allowed.

In order to further improve the stability of the movement of the ultrasonic transducer 220, an additional mechanical structure may be further arranged in some embodiments of the present invention. For example, the above driving device 240 may further include a guide rail and a sliding block. As shown in FIG. 4, the guide rail 344 may be fixedly arranged in the frame 322 in any manner, for example, fixed by screws. For example, the guide rail 344 may be fixed to two side walls of the frame 322 in a manner of being substantially parallel to the above lead screw 342. Correspondingly, the sliding block 343 may be fixedly connected to the motor 341. The fixed connection may be established when the sliding block and the motor are integrally formed, or welded together or detachably connected in any other manner. The sliding block 343 and the guide rail 344 are configured to be in a sliding connection. Therefore, it is possible to perform guiding during the movement of the ultrasonic transducer 220. Such an arrangement ensures that the ultrasonic transducer 220 moves more stably in the process of performing automatic scanning, and it is not prone to other conditions that affect the quality of the ultrasonic imaging, such as side-to-side oscillations or up-and-down vibrations.

Figure 5:
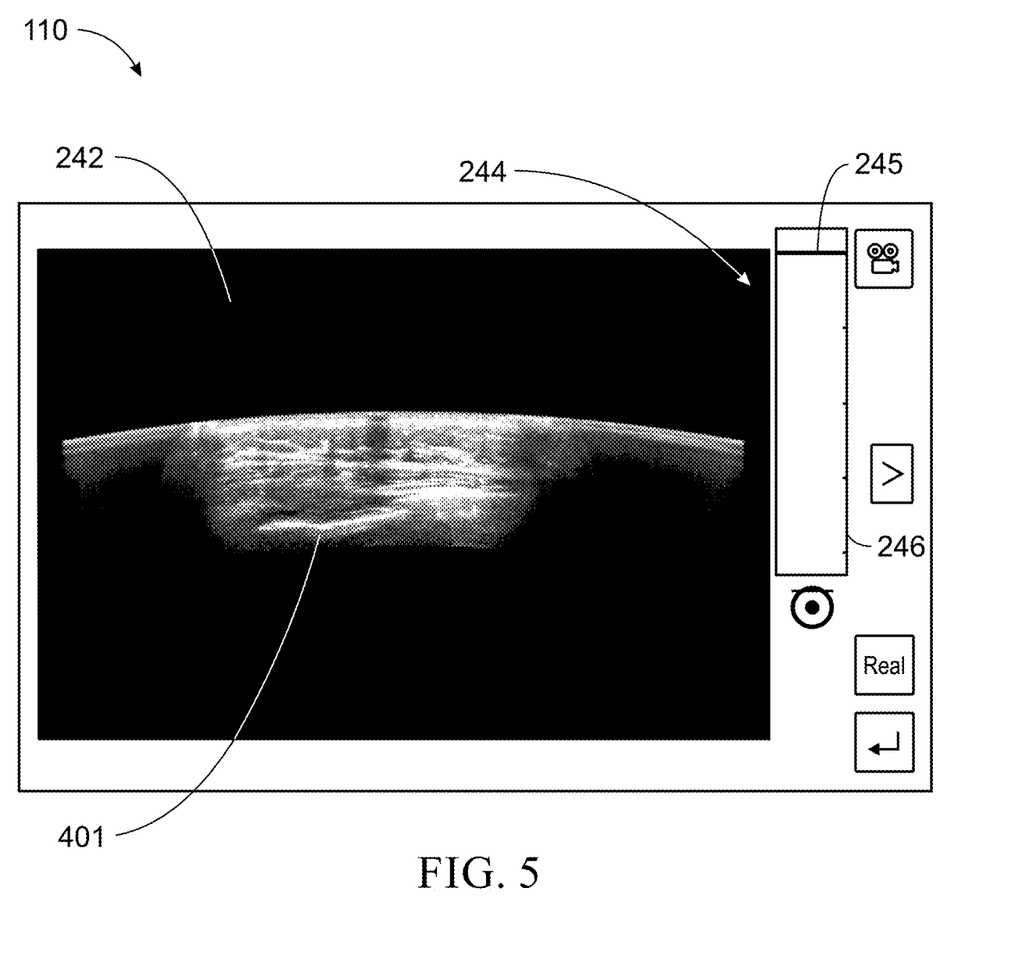
FIG. 5 is a schematic diagram of a user interface and a user input unit on a display according to some embodiments of the present invention.

Referring to FIG. 5, a schematic diagram of the user interface 242 and the user input unit 244 on the display 110 according to some embodiments of the present invention is shown. In some embodiments, a portion of the display 110 may include the user interface 242. The user interface 242 may include a portion for displaying an ultrasonic image 401. Additionally, another portion of the display 110 may further include the user input unit 244. The user input unit 244 may be a portion of a touch screen display, for example, it may be arranged anywhere that does not overlap the user interface 242. A position thereof may be fixed, for example, on a right side of the touch screen, or may be adjustable, for example, a user may drag the user input unit as required. In some other embodiments, the user input unit 244 may overlap the user interface 242 in certain states. For example, the user input unit is arranged above the user interface 242. It should be noted that the user input unit 244 may be integrated on the touch screen of the display 110, as shown in FIG. 5. The user input unit may also be independent of the display 110, for example, the user input unit may be a touch screen structure arranged separately. Details will not be described herein again.

The user input unit 244 may receive an instruction input by a user, for example a touch gesture, and then perform further operations. Usually, after single ultrasonic scanning is completed, a set of lots of ultrasonic images will be produced and displayed on the display 110. Since the number of the ultrasonic images is huge, the display 110 usually displays one ultrasonic image in the set of ultrasonic images. At this time, the user, by controlling the user input unit 244, may select an ultrasonic image that needs to be displayed from the set of ultrasonic images. For example, the user input unit 244 may be configured to include an image position indicating unit 245 and a stroke display unit 246. A shape of the image position indicating unit 245 may be arbitrary, for example, a shape of a straight line segment as shown in FIG. 5. Accordingly, the stroke display unit 246 may have the shape of a long strip. The image position indicating unit 245 may be clicked and dragged by the user within upper and lower ranges of the stroke display unit 246. In this way, when the user drags the image position indicating unit 245, a corresponding ultrasonic image 401 also changes accordingly.

In some embodiments, a position of the image position indicating unit 245 within the range of the stroke display unit 246 may be configured to correspond to a position of the ultrasonic transducer 220 within the range of the frame 322 in FIG. 3. That is, when the ultrasonic transducer 220 moves to a certain side of the frame 322 (e.g., a leftmost side) and imaging begins, a first image generated by the system may correspond to an ultrasonic image to which the image position indicating unit 245 at a certain end (e.g., a lowermost end) of the stroke display unit 246 corresponds. Correspondingly, as the ultrasonic scanning is completed, the ultrasonic transducer 220 will move to another side of the frame 322 (e.g., a rightmost side), and at this time, the system generates a last image which may correspond to an ultrasonic image to which the image position indicating unit 245 at another end (e.g., an uppermost end) of the stroke display unit 246 corresponds. Therefore, the user input unit 244 is enabled to select a corresponding ultrasonic image acquired at any specific position of a plurality of positions of the ultrasonic transducer. Such correspondence facilitates the user to review all the acquired ultrasonic images after the ultrasonic scanning is completed, and can clearly learn to which position of an entire tissue to be scanned an ultrasonic image 401 viewed currently corresponds.

The user, by controlling the user input unit 244, may check the ultrasonic images. When it is found that there are unsatisfactory images or images that need to be emphatically observed (e.g., suspected pathology) in the ultrasonic images, it is usually necessary to rescan the tissue to be scanned. The entire scanning process requires a rerun of the ultrasonic transducer 220 for a whole cycle within the frame of the scanning assembly 108, and thus it would take a lot of time again. In order to solve this problem, in some embodiments of the present invention, the user input unit 244 is further configured to send an input signal while selecting an ultrasonic image 401 to which a specific position corresponds. The input signal may be configured to control movement of the ultrasonic transducer 220, driven by the driving device 240, to the specific position. The so-called specific position means a position of the ultrasonic transducer to which a current ultrasonic image displayed by the display corresponds. Such a configuration enables the ultrasonic transducer 220 to correspond to the ultrasonic image displayed by the display all the times, when the user checks the entire set of ultrasonic images. When the user has a need for rescanning, the ultrasonic transducer 220 may directly work and the re-acquired image directly corresponds to a position required by the user without rescanning from an initial position. This greatly shortens a time required for secondary scanning. It should be noted that an input signal of the user input unit 244 may act on the driving device 240 in any manner. For example, as shown in FIG. 2, the above input signal may directly act on the scanning assembly 108, e.g., a control circuit, for controlling the driving device 240, in the scanning assembly 108. Alternatively, the above input signal may act on the scanning processor 210, and send a control signal to the scanning assembly 108 through the scanning processor 210. Details will not be described herein again.

Further, the above input signal may be configured to control generation of a new ultrasonic image. Specifically, the input signal may be further configured to: control the ultrasonic transducer 220 to resend an ultrasonic signal and acquire an echo signal after the ultrasonic transducer 220 moves to the specific position, thereby further causing the processor to generate an updated ultrasonic image corresponding to the specific position based on the echo signal. Such a configuration can ensure that when a user finds that an ultrasonic image at a specific position needs to be rescanned, the scanning assembly may be controlled to rescan the specific position simply through an input signal of the user input unit 244, without scanning an entire tissue to be scanned, which saves time to a greater extent. Furthermore, as described above, the ultrasonic transducer 220 moves with a specific position of the user corresponding to a specific ultrasonic image in the set of ultrasonic images, and thus rescanning requires only sending an ultrasonic signal directly at the position, without further controlling the ultrasonic transducer to move to the specific position.

It should be noted that the input signal that controls the scanning assembly to perform ultrasonic scanning again on the specific position may be automatic, for example, synchronous with the input signal for the ultrasonic transducer 220 moving to the specific position under driving of the driving device 240. In such an arrangement, the user may directly obtain an updated ultrasonic image at a specific position. In some other embodiments, the input signal controlling the scanning assembly to perform ultrasonic scanning again on the specific position may need to be additionally controlled. For example, after a user stays at an ultrasonic image interface to which a certain specific position corresponds for a certain time, or when the user input device receives an operation instruction of the user (e.g., double click, hold, etc. which are different from instructions that control the ultrasonic transducer to move), such a configuration may ensure that the user performs ultrasonic scanning when needing to update an ultrasonic image to which a specific position corresponds.

Figure 6:
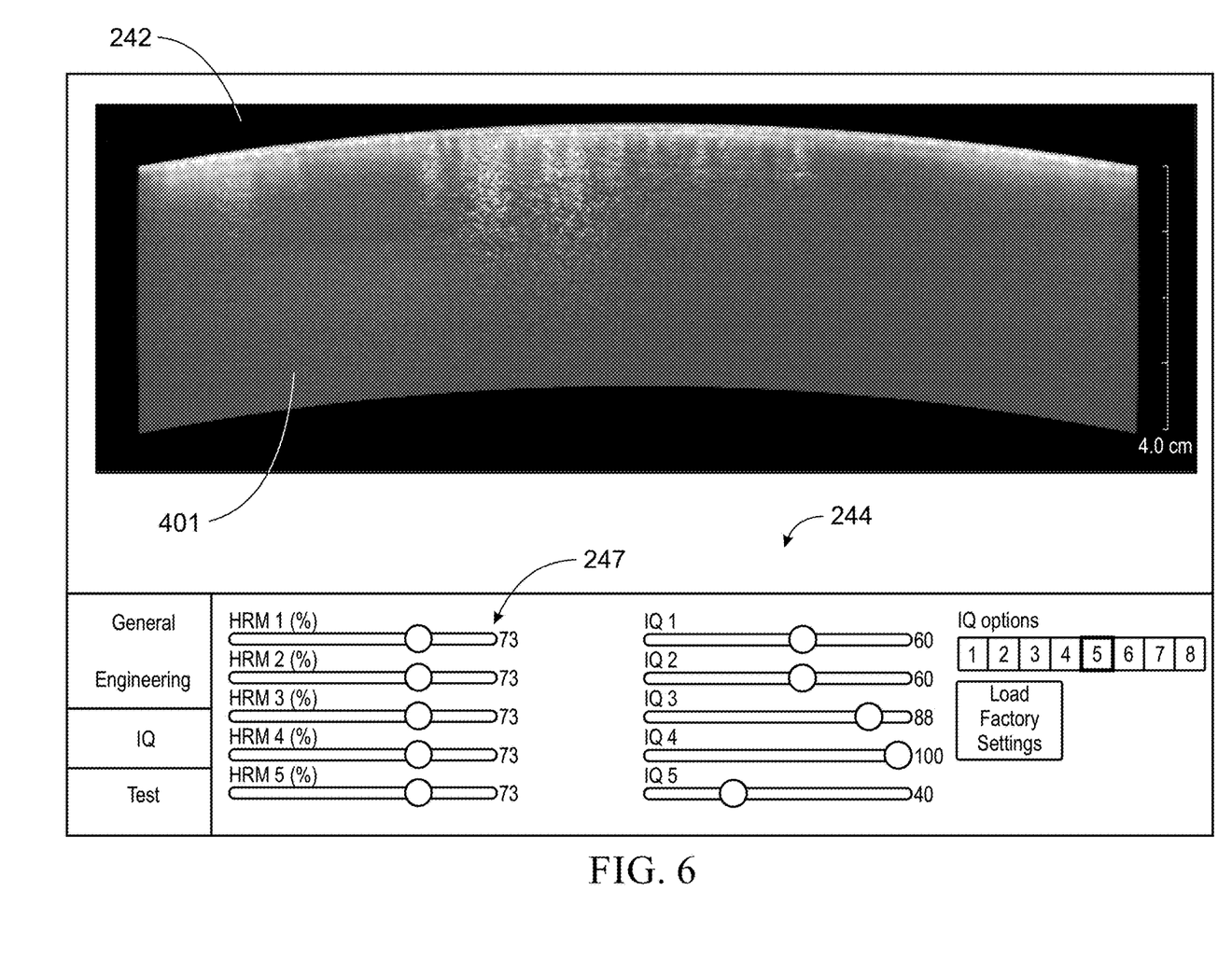
FIG. 6 is a schematic diagram of a user interface and a user input unit on a display according to some other embodiments of the present invention.

The user input unit 244 may further integrate other functions to facilitate user operations. Referring to FIG. 6, a schematic diagram of the user interface 242 and the user input unit 244 on the display according to some other embodiments of the present invention is shown. In addition to being configured with the function of providing an input signal described above, the user input unit 244 may also be configured with an ultrasonic image parameter adjustment function. For example, as shown in FIG. 6, when a user selects an ultrasonic image 401 to which a certain specific position corresponds, parameters of the ultrasonic image 401 may be further adjusted. The adjustment function may be implemented by an image parameter adjustment unit 247. The image parameter adjustment unit 247 may be invoked by a user clicking on a specific position of the touch screen (e.g., some menus shown in the lower right corner of FIG. 6). Further, the image parameter adjustment unit 247 may include an adjustment module for parameters such as image contrast, and image grayscale value. Therefore, the user is facilitated to obtain an ultrasonic image most suitable for observation.

Figure 7:
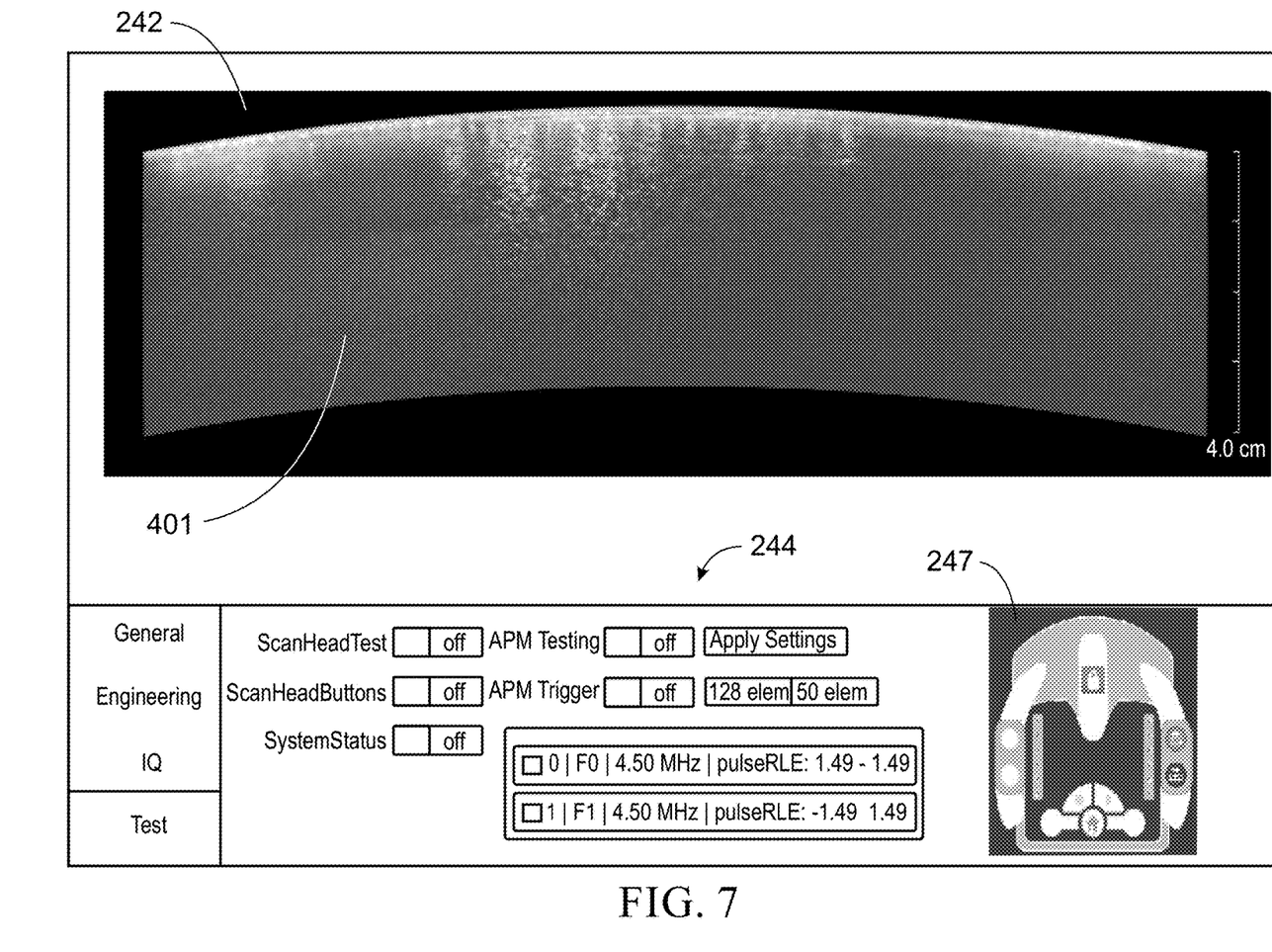
FIG. 7 is a schematic diagram of a user interface and a user input unit on a display according to some other embodiments of the present invention.

Further, the user input unit 244 may further include a function of controlling the scanning assembly 108. Referring to FIG. 7, a schematic diagram of the user interface 242 and the user input unit 244 on the display according to some other embodiments of the present invention is shown. In this embodiment, the user input unit 244 may be configured to have a function of adjusting scanning parameters of the scanning assembly 108. For example, as shown in FIG. 7, when a user selects an ultrasonic image 401 to which a certain specific position corresponds and needs to rescan the specific position, the parameters of the scanning assembly 108 may be directly adjusted as required. In some embodiments, scanning assembly 108 mapping 247 may be configured on a user input unit 244 interface. The mapping may integrate various functions of physical keys on the scanning assembly 108, e.g., a pressure adjustment function, a scanning assembly 108 locking function, etc., corresponding to the functions of the scanning assembly 108 shown above. In this way, by clicking on the scan assembly mapping 247, controlling the scan assembly 108 can be achieved without further manually operating the scan assembly 108. This function may cooperate with the aforementioned function of an input signal for controlling the ultrasonic transducer to rescan so as to achieve rapid adjustment of the parameters of the scanning assembly 108, thereby facilitating ultrasonic imaging again.

Figure 8:
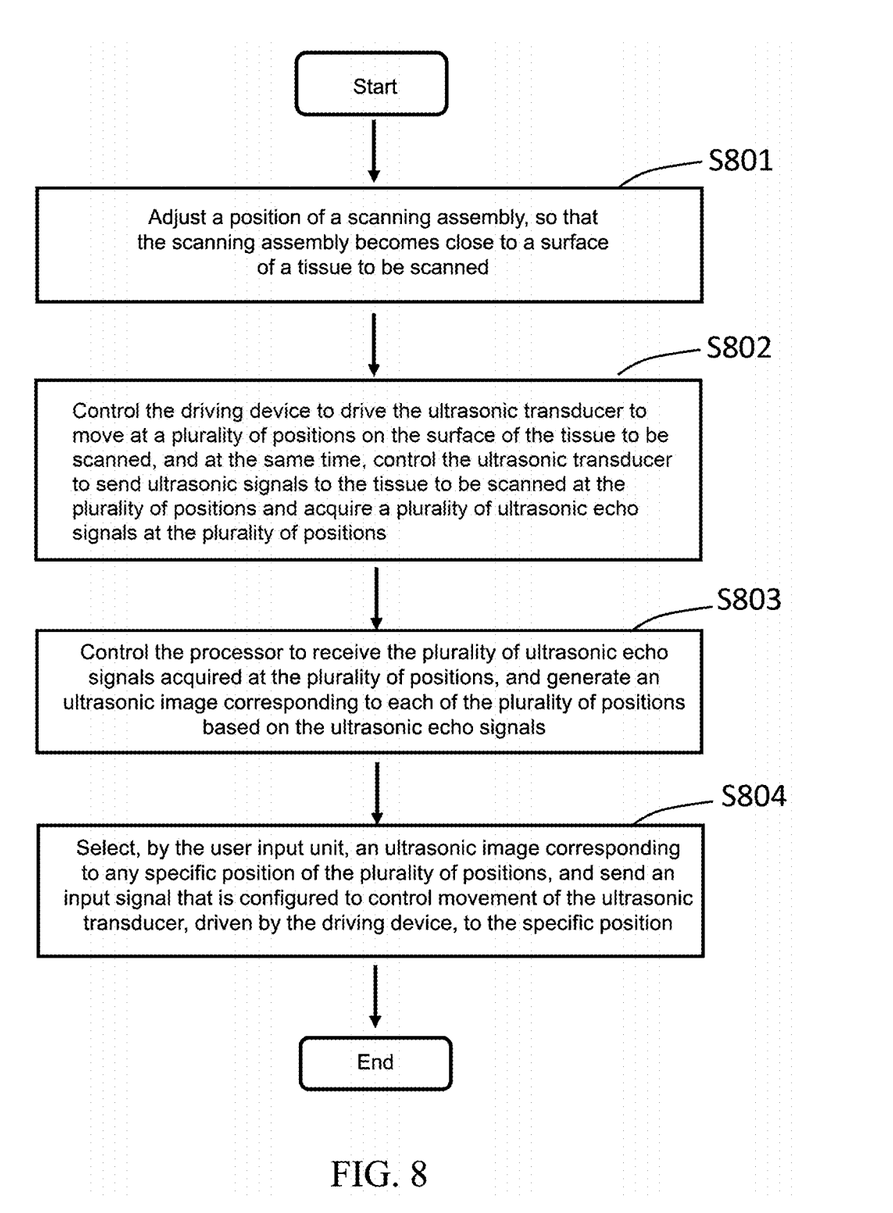
FIG. 8 is a flowchart of an ultrasonic imaging method according to some embodiments of the present invention.

Some embodiments of the present invention further provide an ultrasonic imaging method. The ultrasonic imaging method may rely on the ultrasonic imaging system according to any of the preceding embodiments. Referring to FIG. 8, a flowchart of the ultrasonic imaging method according to some embodiments of the present invention is shown.

Referring first to step S801, the step including adjusting a position of the scanning assembly so that the scanning assembly becomes close to a surface of a tissue to be scanned. This process may be performed by a user holding a handle, as shown in FIG. 3, of the scanning assembly 108, and after the scanning assembly becomes close to the surface of the tissue to be scanned, a weight adjustment button on the scanning assembly 108 may be adjusted to adjust a pressure of the film assembly against the tissue to be scanned. Therefore, conditions most favorable for imaging are obtained.

Step S802 is further performed. The driving device is controlled to drive the ultrasonic transducer to move at a plurality of positions on the surface of the tissue to be scanned, and at the same time, the ultrasonic transducer is controlled to send ultrasonic signals to the tissue to be scanned at the plurality of positions, and acquire a plurality of ultrasonic echo signals at the plurality of positions. A driving principle of the driving device has been described above in detail, and will not be repeated again. It should be noted that a speed of movement in this step may be adjusted through a rotational speed of the motor in the driving device, and driving is performed by using a first speed which may be a low speed, thereby facilitating stable imaging of the ultrasonic transducer.

The echo signals acquired by the ultrasonic transducer are transmitted to the processor for processing. Referring to step S803, the processor is controlled to receive the plurality of ultrasonic echo signals acquired at the plurality of positions, and generate an ultrasonic image corresponding to each of the plurality of positions based on the ultrasonic echo signals. The process of processing the echo signals by the ultrasonic transducer and the process of processing the echo signals by the processor may be performed simultaneously, or separately. Ultrasonic images acquired after processing may be displayed on the display described above on the one hand, and may be stored in a memory on the other hand. Alternatively, a user instruction is waited to determine whether to display or store the ultrasonic images.

The processed ultrasonic images may be viewed by the user. Specifically referring to step S804, an ultrasonic image corresponding to any specific position of the plurality of positions is selected by the user input unit, and an input signal, which is configured to control movement of the ultrasonic transducer, driven by the driving device, is sent to the specific position. The specific configuration of the user input unit is described above in detail, and will not be repeated. In this step, the speed of movement of the ultrasonic transducer may be a second speed greater than the first speed. The transducer can be rapidly driven to move to a desired specific position. Therefore, waiting time of a user is further reduced.

In some embodiments, in addition to the steps described above, the method may further include the following steps: controlling, by an input signal of the user input unit, the ultrasonic transducer to resend an ultrasonic signal and acquire an echo signal after the ultrasonic transducer moves to the specific position, and causing the processor to generate an updated ultrasonic image corresponding to the specific position based on the echo signal. This step can ensure that a user directly performs ultrasonic imaging again at the specific position, as required, to acquire satisfactory ultrasonic images. The re-imaging process may be performed automatically, or may be performed again through certain user operations according to the needs of the user. The updated ultrasonic image may be selected to be stored.

The purpose of providing the above specific embodiments is to facilitate understanding of the content disclosed in the present invention more thoroughly and comprehensively, but the present invention is not limited to these specific embodiments. Those skilled in the art should understand that various modifications, equivalent replacements, and changes can also be made to the present invention and should be included in the scope of protection of the present invention as long as these changes do not depart from the spirit of the present invention.

The invention claimed is:

1. An ultrasonic imaging system, comprising:
a scanning assembly comprising a frame defining an opening, a driving device and an ultrasonic transducer, wherein the driving device is configured to translate the ultrasonic transducer to a plurality of positions with respect to the frame during a scanning process, and wherein the ultrasonic transducer is configured to send ultrasonic signals to the tissue to be scanned at the plurality of positions and acquire a plurality of ultrasonic echo signals at the plurality of positions;
a processor configured to receive the plurality of ultrasonic echo signals acquired at the plurality of positions and generate a plurality of ultrasonic images, wherein each of the plurality of ultrasonic images corresponds to a different one of the plurality of positions;
a display for displaying the plurality of ultrasonic images; and
a user input unit configured for selecting ultrasonic images from the plurality of ultrasonic images for review on the display in response to receiving instruction inputs from a user after the plurality of images have been generated, wherein the user input unit is further configured to send input signals to the driving device in response to receiving instruction inputs from the user, wherein the input signals control the driving device to translate the ultrasonic transducer to a specific position of a current ultrasonic image being displayed on the display, wherein the specific position and the current ultrasonic image corresponds to one of the different plurality of positions of the corresponding plurality of ultrasonic images;
the scanning assembly configured to rescan the specific position based on the user input unit selection received by the processor.

2. The ultrasonic imaging system according to claim 1, wherein
the user input unit comprises a touch screen.

3. The ultrasonic imaging system according to claim 1, wherein
the display comprises a touch screen;
the user input unit comprises a portion of the touch screen.

4. The ultrasonic imaging system according to claim 1, wherein the input signal is further configured to:
control the ultrasonic transducer to resend an ultrasonic signal and acquire an echo signal after the ultrasonic transducer moves to the one of the plurality of positions, and cause the processor to generate an updated ultrasonic image corresponding to the one of the plurality of positions based on the echo signal.

5. The ultrasonic imaging system according to claim 1, wherein
the driving device comprises a motor and a lead screw, the lead screw is arranged in the frame, and the motor is fixedly connected to the ultrasonic transducer and movably connected to the lead screw to drive the ultrasonic transducer to move.

6. The ultrasonic imaging system according to claim 5, wherein
the driving device further comprises a guide rail and a sliding block, the guide rail is fixedly arranged in the frame, the sliding block is fixedly connected to the motor, and the guide rail is slidably connected to the sliding block and is configured to perform guiding when the ultrasonic transducer moves.

7. The ultrasonic imaging system according to claim 1, further comprising:
a film assembly comprising an outer frame and a film, the film being fixedly arranged in the outer frame that is detachably connected to the scanning assembly, in an ultrasonic imaging process of the ultrasonic imaging system, one surface of the film being at least partially in contact with the ultrasonic transducer, and another surface of the film being at least partially in contact with the tissue to be scanned.

8. The ultrasonic imaging system according to claim 1, wherein
the user input unit is further configured for adjusting parameters of an ultrasonic image corresponding to the specific position.

9. The ultrasonic imaging system according to claim 1, wherein
the user input unit is further configured for adjusting scanning parameters of the scanning assembly.

10. The ultrasonic imaging system of claim 1, wherein the user input unit is configured to receive an additional instruction input selecting a different one of the plurality of ultrasonic images for display on the display, wherein the different one of the plurality of images corresponds to a different one of the plurality of positions, wherein the user input unit is configured to send an additional input signal to the driving device in response to receiving the additional instruction input, wherein the additional input signal controls the driving device to translate the ultrasonic transducer to the different one of the plurality of positions corresponding to the different one of the plurality of ultrasonic images.

11. The ultrasonic imaging system of claim 1, wherein the user input unit is configured to receive a plurality of instruction inputs, where each of the plurality of instruction inputs selects a different one of the plurality of ultrasonic images for display on the display, and wherein the user input unit if configured to control the driving device to position the ultrasonic transducer so it corresponds to the currently displayed one of the plurality of ultrasonic images.

12. The ultrasonic imaging system of claim 1, wherein the user input unit is further configured to include an image positioning indicating unit and a stroke display unit, where a position of the imaging positioning indicating unit within a range of the stroke display unit correspond to a position of the ultrasonic transducer within a range of the frame.

13. The ultrasonic imaging system of claim 12, wherein the instruction input for selecting the one of the plurality of ultrasonic images comprises dragging the image positioning unit within an upper range and a lower range of the stroke display unit.

14. An ultrasonic imaging method comprising:
  bringing a scanning assembly close to a surface of a tissue to be scanned, the scanning assembly comprising a frame defining an opening, a driving device, and an ultrasonic transducer;
  controlling the driving device to translate the ultrasonic transducer to a plurality of positions with respect to the frame during a scanning process, controlling the ultrasonic transducer to send ultrasonic signals to the tissue to be scanned at the plurality of positions and acquire a plurality of ultrasonic echo signals at the plurality of positions;
  receiving the plurality of ultrasonic echo signals with a processor and generating a plurality of ultrasonic images, wherein each of the plurality of ultrasonic images corresponds to a different one of the plurality of positions;
  receiving, with the user input unit, an instruction input for displaying one of the plurality of ultrasonic images on a display, where the one of the plurality of images corresponds to one of the plurality of positions;
  displaying the one of the plurality of ultrasonic images on the display; and
  automatically sending, from the user input unit, an input signal to the driving device in response to receiving the instruction input, wherein the input signals control the driving device to translate the ultrasonic transducer to a specific position of a current ultrasonic image being displayed on the display, wherein the specific position and the current ultrasonic image corresponds to one of the different plurality of positions of the corresponding plurality of ultrasonic images;
  rescanning of the specific position with the scanning assembly based on the user input unit selection received by the processor.

15. The ultrasonic imaging method according to claim 14, further comprising:
  controlling the ultrasonic transducer to send an additional ultrasonic signal and acquire an additional echo signal after the ultrasonic transducer moves to the one of the plurality of positions in response to the input signal sent from the user input unit, and causing the processor to generate an updated ultrasonic image corresponding to the one of the plurality of positions based on the additional echo signal.

16. The ultrasonic imaging method of claim 14, wherein the method further comprises:
  receiving, with the user input unit, an additional instruction input for displaying a different one of the plurality of ultrasonic images for display on the display, wherein the different one of the plurality of ultrasonic images corresponds to a different one of the plurality of positions;
  displaying the additional one of the plurality of ultrasonic images on the display in response to receiving the additional instruction input; and
  automatically sending, from the user input unit, an additional input signal to the driving device in response to receiving the additional instruction input, where the additional input signal controls the driving device to translate the ultrasonic transducer to the different one of the plurality of positions corresponding to the different one of the plurality of ultrasonic images displayed on the display.

* * * * *